United States Patent [19]
Netherly

[11] Patent Number: 6,007,532
[45] Date of Patent: Dec. 28, 1999

[54] METHOD AND APPARATUS FOR DETECTING LOSS OF CONTACT OF BIOMEDICAL ELECTRODES WITH PATIENT SKIN

[75] Inventor: Samuel G. Netherly, Afton, Minn.

[73] Assignee: 3M Innovative Properties Company, St. Paul, Minn.

[21] Appl. No.: 08/924,037

[22] Filed: Aug. 29, 1997

[51] Int. Cl.[6] ................................. A61B 17/39
[52] U.S. Cl. ................................. 606/35; 606/32
[58] Field of Search ........................ 606/32, 35

[56] References Cited

U.S. PATENT DOCUMENTS

| | | |
|---|---|---|
| 3,601,126 | 8/1971 | Estes . |
| 4,092,986 | 6/1978 | Schneiderman . |
| 4,102,341 | 7/1978 | Ikuno et al. . |
| 4,141,351 | 2/1979 | James et al. . |
| 4,200,104 | 4/1980 | Harris . |
| 4,231,372 | 11/1980 | Newton . |
| 4,281,373 | 7/1981 | Mabille . |
| 4,321,926 | 3/1982 | Roge . |
| 4,416,276 | 11/1983 | Newton et al. . |
| 4,416,277 | 11/1983 | Newton et al. . |
| 4,524,087 | 6/1985 | Engel . |
| 4,539,996 | 9/1985 | Engel . |
| 4,658,819 | 4/1987 | Harris et al. . |
| 4,727,874 | 3/1988 | Bowers et al. . |
| 4,754,757 | 7/1988 | Feucht . |
| 4,793,362 | 12/1988 | Tedner . |
| 4,848,335 | 7/1989 | Manes . |
| 4,848,353 | 7/1989 | Engel . |
| 4,860,745 | 8/1989 | Farin et al. . |
| 4,922,210 | 5/1990 | Flachenecker et al. . |
| 4,969,885 | 11/1990 | Farin . |
| 5,012,810 | 5/1991 | Strand et al. . |
| 5,080,099 | 1/1992 | Way et al. . |
| 5,087,257 | 2/1992 | Farin et al. . |
| 5,215,087 | 6/1993 | Anderson et al. . |
| 5,232,838 | 8/1993 | Nelson et al. . |
| 5,362,420 | 11/1994 | Itoh et al. . |
| 5,422,567 | 6/1995 | Matsunaga . |
| 5,702,386 | 12/1997 | Stern et al. ........................ 606/34 |
| 5,800,426 | 9/1998 | Taki et al. ........................ 606/32 |

FOREIGN PATENT DOCUMENTS

| | | |
|---|---|---|
| WO 96/19152 | 6/1996 | WIPO . |
| WO 97/37719 | 10/1997 | WIPO ........................ A61N 1/04 |

*Primary Examiner*—Linda C. M. Dvorak
*Assistant Examiner*—Roy Gibson
*Attorney, Agent, or Firm*—Eloise J. Maki

[57] ABSTRACT

A method of monitoring the contact of a biomedical electrode to skin of a patient is disclosed, where at least two different frequencies are employed to periodically monitor total contact impedance of the electrode. The ratio of the change of the total contact impedances over time can then be monitored to indicate the amount of lift of the biomedical electrode from human skin to which it is supposed to be adhered. Lift of any portion of the electrode from contact with skin of a patient can be monitored more easily than using conventional Contact Quality Monitoring circuitry and "split plate patient plates."

4 Claims, 3 Drawing Sheets

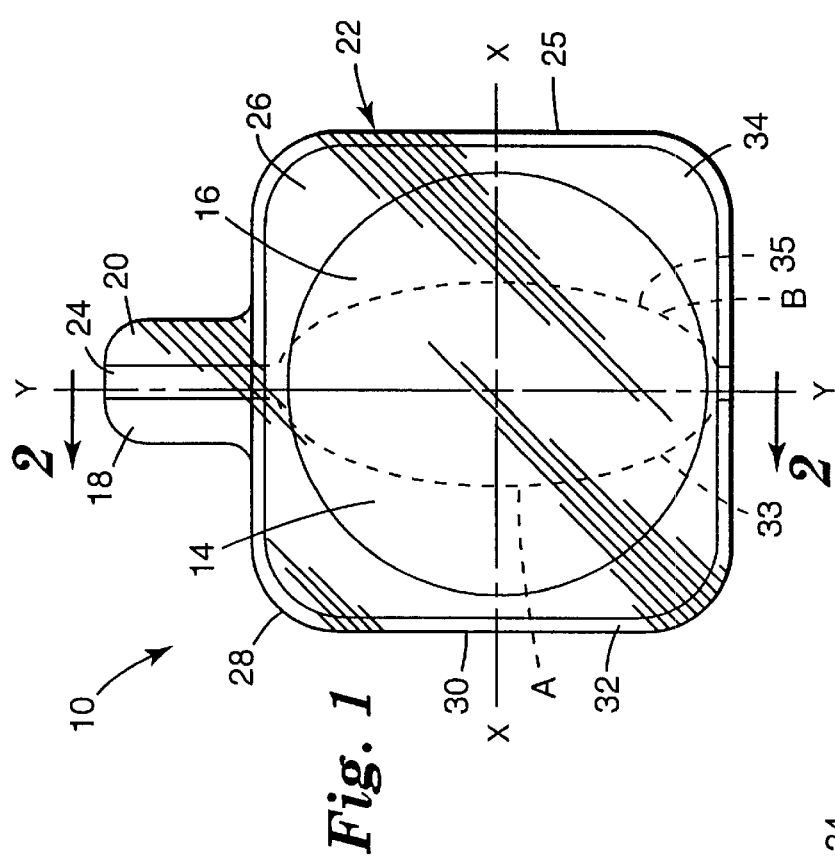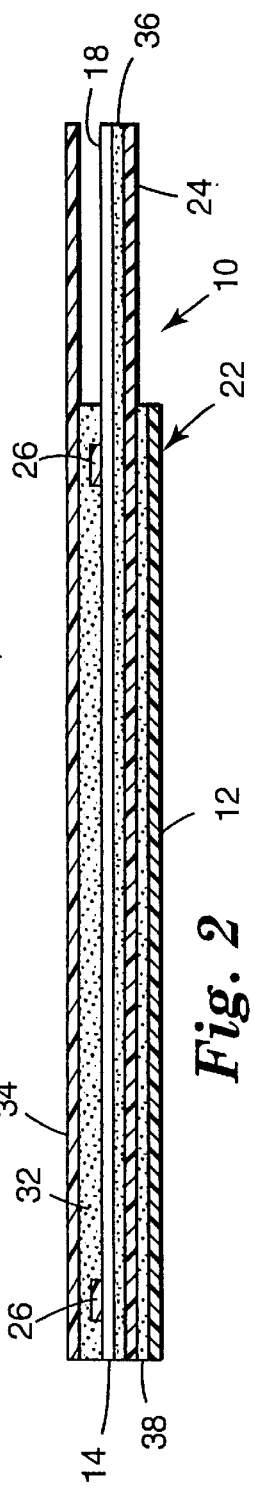

METHOD AND APPARATUS FOR DETECTING LOSS OF CONTACT OF BIOMEDICAL ELECTRODES WITH PATIENT SKIN

FIELD OF INVENTION

This invention concerns a method and apparatus for detecting loss of contact with patient skin of biomedical electrodes, particularly dispersive return electrodes or "patient plates" having lossy dielectric properties, during delivery of electrical current to a patient, particularly during electrosurgery. More particularly, the invention concerns a method of determining whether an electrosurgical patient plate has accidentally lifted in any location from a patient's skin.

BACKGROUND OF INVENTION

Biomedical electrodes are used in a variety of applications and are configured to operate according to the size, type, and direction of current flowing into or out of a body of a patient.

Dispersive electrodes are used in electrosurgery. In modem surgical practice, there are many times when electrosurgery is more preferable than the use of the traditional scalpel. In electrosurgery, cutting is performed by an intense electrical current passing through a cutting electrode. The surgeon directs this current to exactly where cutting is required by wielding the cutting electrode, which because of its cylindrical shape and the way it is held in the hand is commonly called an "electrosurgical pencil". By activating controls which change the characteristics of the electrical current being sent to the pencil by an electrosurgical generator, the surgeon can use the pencil either to cut or to coagulate areas of bleeding. This makes electrosurgery particularly convenient when surgery requiring extra control of blood loss is being performed. Because of concerns to minimize the transmissions of blood-borne illnesses between health care patients and health care providers, in both directions, electrosurgery is becoming increasingly important.

In electrosurgery, as in all situations where electrical current is flowing, a complete circuit must be provided to and from the current source. In this case, the current that enters the body at the pencil must leave it in another place and return to the generator. It will readily be appreciated that when current enough to deliberately cut is brought to the body of a patient in one place, great care must be taken that unintentional damage is not also done to the patient at the location where that current is leaving the body. The task of collecting the return current safely is performed by a dispersive electrode.

A dispersive electrode performs this task by providing a large surface area through which the current can pass; the same current which was at cutting intensity when focused at the small surface area at the tip of the pencil is relatively harmless, with the goal of being painless to the patient, when spread out over the large surface area of the dispersive electrode.

Unfortunately, any geometry of the large surface area has an edge and perhaps distinct comers or junctions where "edge effects", caused by increased current density at those locations, can have a maximum temperature rise during usage by the patient making such dispersive electrode or cardiac stimulating electrode most uncomfortable to the patient.

The same difficulties concerning edge effect also are present in cardiac stimulating electrodes, such as those used for defibrillation, external pacing, or cardioversion. For a patient already in some discomfort or ill health, pain sensed by the very medical device intended to treat the patient is disconcerting at best.

Safety systems for the electrosurgical patient plates use "Contact Quality Monitor" ("CQM") circuits. All CQM systems currently in use are based on a single design, involving the use of a split patient plate. The reason that the plate must be split is to create two separate conductors that are not electrically joined, unless the electrode is placed on the skin of a patient. If it is indeed properly placed, then a small current can be passed by the generator down one wire of the cable connecting the generator to one of the conductors on the split plate. From there, the current then passes into the flesh of the patient, crosses over to the other conductor of the split plate, and then back through the other wire of the connecting cable to the generator. By analyzing this current, the generator is able to measure an impedance for the combined circuit of the cable, both halves of the split plate, and the patient.

This impedance must be within a certain pre-determined range which assures that the plate has been placed on the patient and that it is in full or nearly full contact with the skin of the patient.

One other point should be made about these CQM systems, and the current that is used by them to determine when the plate is in good contact with the patient: The CQM current should not be confused with the surgical current, which does all the cutting and coagulating. The CQM current is a lower frequency (typically about 39–350 KHz) than the surgical current frequency (typically about 500–1000 KHz), and is hundreds of times smaller in both voltage and amperage than the surgical current (about 1 mV and 1 mA vs. about 500 V and 2 A, respectively).

It is also important to note that the CQM system is only active when the surgical current is not flowing, since the surgical current is so powerful that it would burn out the CQM circuit if the CQM circuit were active while the surgical current was flowing.

The CQM system, first introduced in 1984, has become the industrial safety standard for electrosurgery. Further disclosure of the CQM system is found in U.S. Pat. Nos. 4,200,104 (Harris); 4,231,372 (Newton); 4,416,277 (Newton et al.); 4,416,276 (Newton et al.); and 4,848,335 (Manes).

In addition to the CQM system, additional systems have been developed. One of them is the "NESSY" system sold by Erbe, Inc. of Tübingen, Germany. The system has two separate circuits, with the first circuit being the standard CQM type described above. The second circuit, however, is unique to the Erbe generator and actually measures the surgical current that is flowing through both halves of the split plate. The amperage flowing in the two halves of the plate is compared, and if there is too great a difference between the current levels the generator will alarm and shut down.

Another attempt to provide protection for an electrosurgery patient is disclosed in U.S. Pat. No. 5,080,099 (Way et al.). In these patents are disclosed a triple plate electrode in order to provide a measure of "peel back" of the patient plate from the patient. But these electrodes disclosed in the Way et al. patent were quite complex to manufacture and use.

SUMMARY OF INVENTION

The present invention determines whether an electrosurgical patient plate has accidentally lifted from a patient's skin. This method is an unexpected and significant improvement over the sensitivity and accuracy of any Contact Quality Monitoring or "NESSY" system used in an electrosurgical generator today. The present invention does not necessarily require the use of a split patient plate.

However, the present invention does require the use of a patient plate with a lossy dielectric region at its periphery and is not applicable to standard resistive or capacitive plates. Nonlimiting examples of a patient plate with a lossy dielectric region at its periphery include those biomedical electrodes disclosed in copending, coassigned, U.S. patent application Ser. No. 08/644,799; 08/628,182; 08/644,798 (all Netherly or Netherly et al.), the disclosures of which are incorporated by reference herein.

One aspect of the present invention is the use of a lossy dielectric plate in conjunction with electronic circuitry that is uncomplicated to initiate and employ. The method and apparatus of the present invention utilizes the Netherly patient plate, which is unique in that it does not pass current through its surface in the same way at all points.

At the comers and the very outer border of the lossy dielectric surface, the current emerging from the patient (or introduced to a patient in the case of a stimulating or pacing electrode) is forced to pass through the lossy dielectric layer in a "more capacitive than resistive" way.

Another aspect of the invention is a method of determining small amounts of lift of a biomedical electrode from a patient's skin, provided that biomedical electrode has at least part of its conductor area coated with a lossy dielectric material. The method of determining lift comprises measuring the contact impedance of the biomedical electrode on the patient at two substantially different frequencies upon initial application, and then comparing later pairs of readings with the first pair of impedances measured, wherein a greater change of impedance at the lower frequency point as compared to the upper frequency point indicates that a part of the biomedical electrode coated with lossy dielectric has become detached from the patient's skin.

Another aspect of the present invention is to use the following Equation I to determine the degree of lift of the biomedical electrode:

$$Degree\ of\ Lift = (Z_{f1,t0} - Z_{f1,t1})/(Z_{f2,t0} - Z_{f2,t1})\qquad\text{I}$$

where Z denotes the total contact impedance of the biomedical electrode, f1 denotes the first impedance measurement frequency, f2 denotes the second impedance measurement frequency, t0 denotes the first (or initial) impedance measurement time, and t1 denotes the impedance measurement at some later time. This degree of lift may be represented by digital or analog means on a display on the electrosurgical generator to indicate the relative amount of the biomedical electrode that has lifted since the initial application, and in addition, if this degree of lift exceeds a certain set value, an alarm can be made to sound to audibly alert the user to the degree of lift. In addition to a simple auditory alarm, an increase of the degree of lift beyond a threshold value can also trigger an alarm condition which will disable the generator until the lift of the biomedical electrode from the patient's skin has been corrected.

When such materials are used in the Netherly plate disclosed in copending, coassigned, U.S. patent application Ser. No. 08/644,799; 08/628,182; 08/644,798 (all Netherly or Netherly et al.), one can use Equation I with at least two different frequencies to determine whether changes in impedances occur at different times of measurement: initially and at least one time later.

Preferably, the method and apparatus of the present invention can be used in conjunction with another method disclosed in copending, coassigned, U.S. patent application Ser. No. 08/832835 (Netherly et al.) (Attorney's Docket No. 53324USA5A and incorporated by reference herein) that determines the total phase angle ($\Theta_{Total}$) of current flow, which is equal to the sum of the phase angle of the current flow passing through the lossy dielectric area and the phase angle of the current passing through the bare metal area of the electrode surface near the center of the plate, as seen in Equation II.

$$\Theta_{Total} = [\Theta_{Lossy\ Dielectric} * (Area_{Lossy\ Dielectric}/Area_{Total})] + [\Theta_{Bare\ Metal} * (Area_{Bare\ Metal}/Area_{Total})]\qquad\text{II}$$

Thus, if the relative area of the bare metal and lossy dielectric contacting the patient changed, there would be a net change of the phase angle of the total current flow.

Using the Netherly Patient Plate with coverage of lossy dielectric material from portions of the perimeter inward, and preferably at the comers and edges of the electrical conductor, there is no way that the plate can be peeled up from any direction while keeping the ratio of bare metal area to lossy dielectric area the same. The ratio of lossy dielectric area to bare metal area is significant to both Equations I and II, as seen above.

In relation to Equation I, as the ratio changes, such as lifting off of an edge of a biomedical electrode, the total contact impedance changes. The present invention has found that the change in total contact impedance differs at different frequencies.

With the ability to establish initial, customized values of total contact impedance at two different frequencies and then measure such total contact impedances at those two different frequencies at a later time, then one can monitor if and when the edge or corner of a biomedical electrode begins to lift off the skin of a patient, and preferably how much lift has occurred.

The ratio of change of total contact impedance values at two different frequencies, over time, is independent of any other parameter or property of the biomedical electrode. Further biomedical instrumentation can be calibrated to measure any determined ratio of change of total contact impedances at two different frequencies before an alarm is sounded.

In relation to Equation II, the measure of change of phase angle over change in time is independent of any other parameter or property of the biomedical electrode, because electronic circuitry in the biomedical instrumentation can measure $\delta\Theta/\delta t$ without regard to any other function, property, or parameter of the patient plate. Further the biomedical instrumentation can be calibrated to measure any amount of $\delta\Theta/\delta t$ before an alarm is sounded.

Therefore, by monitoring the ratio of change of the total contact impedances at two different frequencies through any biomedical electrode over time, one can determine whether contact between the biomedical electrode and skin of a patient has changed. While any change in direct contact is not as critical for monitoring biomedical electrodes where any contact could be enough to receive faint electrical signals from the patient, any change in direct contact is critical for any biomedical electrode that requires the delivery of electrical current to a patient or receives from the patient electrical current delivered to the patient in another location.

Another aspect of the present invention is the use of any geometric configuration of electrical conductor on a biomedical electrode, so long as a portion of the electrical conductor is covered with a lossy dielectric material. Thus, using Equation I above, one need not configure a biomedical electrode to have two or more electrical conductors nor need one use either a CQM or NESSY system that relies on differences in current flow between two or more electrical conductors on the surface of the biomedical electrode. The method of the present invention pertains to a split conductor patient plate or a solid conductor patient plate equally well, so manufacturing and performance economies of scale can be achieved regardless of the electrical conductor geometry, but a solid conductor patient plate is easier to make and use.

A feature of the present invention is that, if one were to pass a stream of current through a lossy dielectric Netherly patient plate and monitor the total contact impedances at two different frequencies, the rate of change of the total contact impedances over time should vary relative to each other's value if any portion of the periphery of the plate were lifted. In all cases presently contemplated, a decrease in total contact impedances at two different frequencies should be observed because the area being lifted from any edge would always have more lossy dielectric coating than bare metal lifted.

The two different frequencies can be selected to accommodate a discernible divergence in total contact impedances when measured after initial values are determined. One frequency can range from about 2 MHz to about 100 KHz and preferably from about 1 MHz to about 300 KHz. The second frequency can range from about 100 KHz to about 1 Khz and preferably from about 5 KHz to about 50 KHz. While at least two different frequencies are required, the present invention can use more than two frequencies, particularly if more than type of alarm condition is desired. Also, selection of the frequencies for the method of the present invention should accommodate the ability to quantify the amount of lift of an electrode from a patient's skin. Such quantification can take the form of a series of audible alarms increasing in urgency with increasing edge lift, a digital or analog display of numerical quantity or graphic information, or the like used to provide to health care professionals clear indications of an undesirable condition for the patient.

An advantage of the present invention is that a clearly superior method is provided to measure biomedical electrode lift from skin of a patient, because the most likely source for lift to start would be at the corners of the electrode, and this is precisely where the lossy dielectric coating on an electrical conductor of a Netherly patient plate is located.

Moreover, another advantage of the present invention is the ability of monitoring lift of a solid, single conductor biomedical electrode, and that this lift could be detected regardless of which way the electrode begins to lift.

Yet another advantage of the present invention is the ability to combine the method and apparatus of the present invention with another method of monitoring edge lift as disclosed in copending, coassigned, U.S. patent application Ser. No. 08/832835 (53324USA5A).

Thus, the invention can be expressed in a variety of ways:

The invention includes a method of detecting loss of contact between a biomedical electrode and skin of a patient, comprising the steps of (a) detecting total contact impedance of the electrode at two different frequencies to establish two initial contact impedances; (b) detecting the total contact impedances of the electrode at the same frequencies as in step (a) at at least one later time to establish two differences in total contact impedance, one difference for each frequency; and (c) sounding an alarm when the ratio of the two differences exceeds a predetermined amount.

The invention also includes a method of quantifying lift off of a biomedical electrode from skin of a patient, by the use of the equation:

$$\text{Degree of Lift} = (Z_{f_1 t_0} - Z_{f_1 t_1}) / Z_{f_2 t_0} - Z_{f_2 t_1})$$

where Z denotes a total contact impedance of the biomedical electrode, f1 denotes a first impedance measurement frequency, f2 denotes a second impedance measurement frequency, t0 denotes a first (or initial) impedance measurement time, and t1 denotes a impedance measurement at some later time, comprising the steps of (a) measuring two initial total contact impedances using two different frequencies, (b) measuring two later time total contact impedances using the same two frequencies as in step (a) and using the equation to obtain a ratio of change of the two total contact impedances; and (c) sounding an alarm when the ratio of change of the two total contact impedances exceeds a certain set value.

The invention also includes a method of determining the amount of skin contact between a biomedical electrode and skin of a patient, comprising the steps of (a) measuring the ratio of the change of two total contact impedances, measured at different frequencies, over time for an energized biomedical electrode; and (b) sounding an alarm when the ratio of the change of the difference in total contact impedances over time exceeds a predetermined amount.

The invention further includes an apparatus for detecting loss of contact between a biomedical electrode and skin of a patient, comprising (a) a biomedical electrode having an electrical conductor having at least a portion thereof having lossy dielectric properties; and (b) means for detecting when a change in the ratio of the change of two total contact impedances measured at two different frequencies over time exceeds a predetermined amount.

Further features and advantages of the invention become apparent using the following drawings to describe the embodiments.

BRIEF DESCRIPTION OF THE DRAWING

The reference numerals refer to like parts in the several views, wherein:

FIG. 1 is bottom perspective view according to one presently preferred embodiment of the dispersive electrode of the present invention;

FIG. 2 is a cross-section view which is taken along section lines 2—2 in FIG. 1;

EMBODIMENTS OF THE INVENTION

Figure 3:
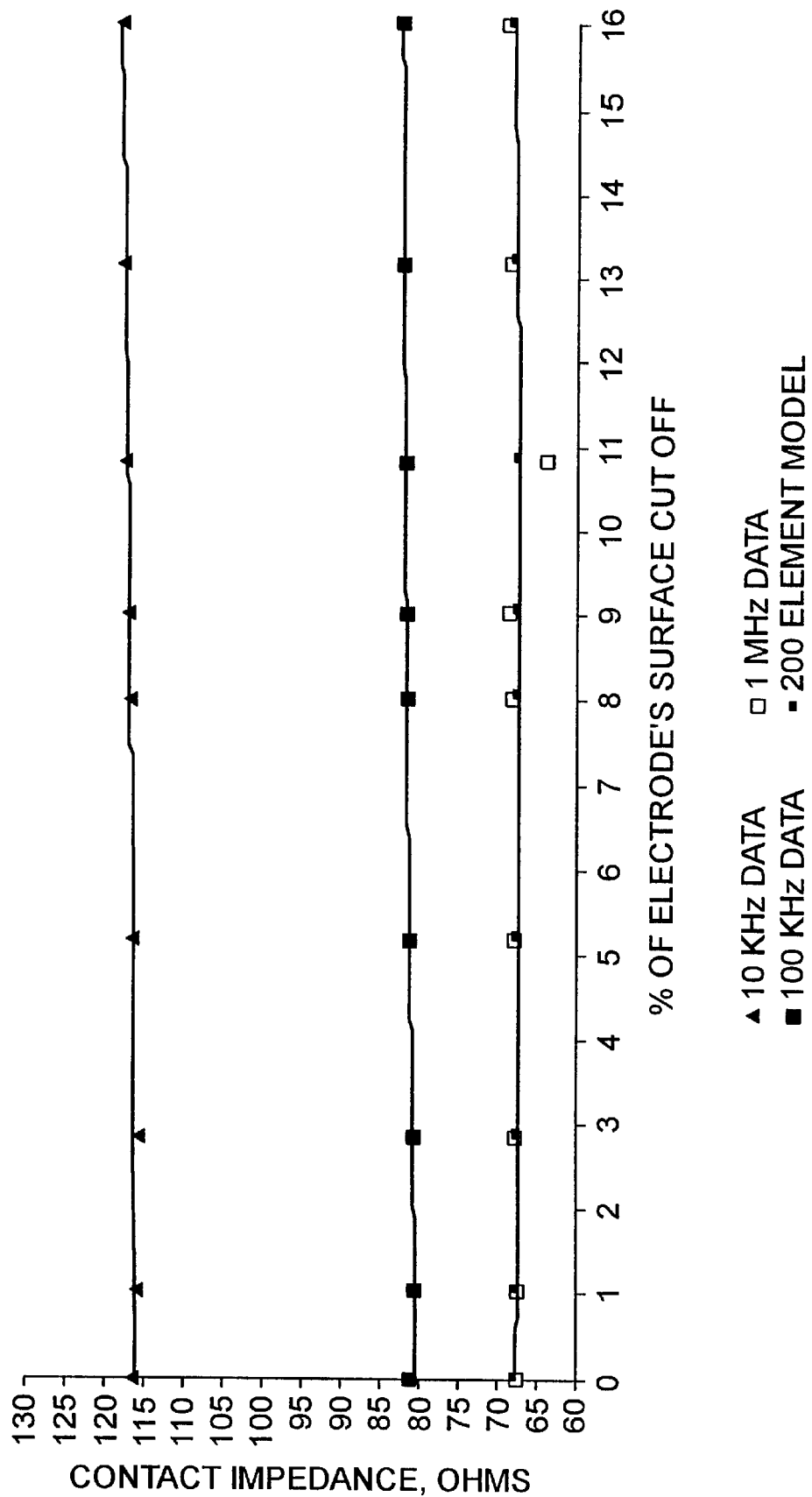
FIG. 3 is a graph showing total contact impedance vs. area of electrode surface for a conventional biomedical electrode using three different frequencies, demonstrating little change for total contact impedances of the various frequencies as the amount of electrode surface area was reduced.

FIG. 1 shows a bottom perspective view of the dispersive biomedical electrode "patient plate" 10. The upper surface of the electrode 10, which is on the far side in this bottom view, can be a flexible and conformable electrically non-conductive backing 12. At least one conductor plate is needed for electrical contact with the body of a patient. In this embodiment, two conductor plates 14 and 16 are present along a longitudinal axis Y—Y matching Section line 2—2, adjacent to, and can be adhered to, the electrically non-conductive backing 12. Two separate conductor plates can be employed because of their usefulness with contact quality monitoring ("CQM") circuitry because the impedance between the conductor plates 14 and 16 is measured by the above mentioned CQM circuits. However, one can also preferably use a single conductor plate that combines conductor plates 14 and 16, the more traditional style of dispersive electrode before CQM circuitry became available.

Each of the two conductor plates 14 and 16 has an extended tab 18 and 20, respectively, extending away from the body contact portion 22 of the electrode 10 for attachment of a cable assembly which connects the electrode 10 to an electrosurgical generator (not shown). When only one conductor plate is present on backing 12, there is only one extended tab. In order to provide more support for the conductor plates 14 and 16, and especially for their respective tabs 18 and 20, a non-conductive support layer 24 can be laminated to the conductor plates. More preferably, the support layer is not needed if manufacturing techniques can be refined.

The region adjacent the exterior edge 25 of the body contact portion 22 of the electrode 10 is covered with a layer 26 of a lossy dielectric material. In the embodiment of FIG. 1, the width of the layer 26 of a lossy dielectric material is widest at the corners 28, and narrowest along the edge 30 midway between the corners. As presently understood, this arrangement of the layer 26 serves best to reduce edge effect at the corners 28 of the dispersive electrode. Further explanation of the use of a lossy dielectric material can be found in copending, coassigned U.S. patent application Ser. No. 08/628,182 (Netherly et al.), the disclosure of which is incorporated by reference herein.

Preferably, the entire body contact portion 22 of electrode 10 is covered with a field 32 of hydrophilic, ionically conductive, pressure sensitive adhesive for simplicity of manufacturing. Many compositions suitable for use for the field 32 of conductive adhesive are transparent, or at least translucent, and have been depicted that way in FIG. 1 for convenience in providing an explanatory drawing. The field 32 of adhesive serves the purpose of adhering the electrode 10 to the body of the patient. When the field 32 is adhesive that is ionically conductive, as it should be for those portions of field 32 contacting plates 14 and 16, the field also has the purpose of transferring the electrosurgical current between the body of the patient and the electrode for electrosurgical currents and between the electrode and the body for total contact impedance analysis according to the present invention.

Each of conductor plates 14 and 16 has an interior edge, 33 and 35 respectively, along the longitudinal axis Y—Y as seen in FIG. 1. Each of edges 33 and 35, or one of them, can be parallel, curvilinear or otherwise non-parallel to the opposing edge in a manner which creates a concave-inward indent relative to the longitudinal axis Y—Y. Preferably, both edges 33 and 35 have curvilinear geometries relative to the longitudinal axis, resulting in a double concave-inward indent symmetrical about the longitudinal axis. More preferably, the double concave-inward indent is also symmetrical about an axis orthogonal to the longitudinal axis, where the second axis is a latitudinal axis X—X substantially equidistant from edges of the body contact portion 22 orthogonal to the longitudinal axis. Most preferably, as seen in FIG. 1, at the point where longitudinal axis Y—Y and latitudinal axis X—X cross orthogonally, the non-conductive gap between edges 33 and 35 is maximal.

It will be seen that at point A which is away from the outside edge 25 of the body contact portion 22 of biomedical electrode 10, the minimum distance separating the conductive plates 14 and 16 is substantially greater than the minimum distance separating the conductive plates at a point B nearer the outside edge of the body contact portion.

FIG. 2 shows a cross-section view of the electrode shown in FIG. 1, taken along section lines 2—2. In this view, a release liner 34 is shown adhered to the field 32 of hydrophilic adhesive. In those portions of electrode 10 where adhesive field 32 contacts one or more conductive plates 14 and 16, the adhesive field 32 is also ionically conductive. This release liner 34 protects the adhesive during shipping and handling and is removed just prior to use. In this view a layer of adhesive 36 is seen adhering the support layer 24 to conductor plate 14 and its extended tab 18. Another layer of adhesive 38 is provided for adhering the electrically non-conductive backing 12 to the other side of the support layer 24.

Electrically non-conductive backing

Electrically non-conductive backing 12 can be electrically insulative, and preferably is very conformable to the various contours of the mammalian body. Many materials can be used for this purpose, as will be apparent to those skilled in the art. In one presently preferred embodiment, a closed-cell foam is considered particularly suitable. One such material is commercially available as Volara brand foam from Voltek, Inc. of Massachusetts. Another is commercially available as a laminate of nonwoven polypropylene and low density polyethylene backing from Milliken of Spartanburg, S.C. The electrically non-conductive backing can have a thickness ranging from about 0.75 mm (0.03 inch) to about 1.5 mm (0.06 inch), and preferably 1.0 mm (0.04 inch).

Conductor plates and support layer

The conductor plates 14 and 16 are conveniently made from metal, preferably in the form of a foil, a metal-containing or graphite-containing coated ink or paint, or a vapor coated metal, and most preferably, aluminum foil. If a support layer 24 is not being used, a thickness of about 0.08 mm (0.0003 inch) is considered preferred. If a support layer 24 is being used, the metal foil or vapor coated metal can be thinner because of the support provided by the support layer. A suitable support layer 24 can be made from polyethylene terephthalate (PET) film, conveniently approximately 0.05 mm (0.002 inch) thick. This allows the aluminum layer to range in thickness between about 0.0075 mm (0.0003 inch) to about 0.025 mm (0.001 inch) and preferably 0.012 mm (0.0005 inch) or allows vapor coated metal to have a minimum thickness of about 1000 Angstroms. An example of vapor coated metal on a substrate is found in PCT Publication No. WO 94/26950, the disclosure of which is incorporated by reference herein.

Hydrophilic adhesive

Each of the hydrophilic adhesives useful in the present invention should be biocompatible with mammalian skin and can be formulated in both ionically conductive and non-conductive embodiments. The ionically conductive adhesives are useful in contact with both mammalian skin and conductor plates 14 and 16. The non-conductive adhesives can be used beyond the perimeter of the conductor plates 14 and 16.

Preferably, if expense of a single field 32 of hydrophilic, ionically conductive, biocompatible, pressure sensitive adhesive is not greater than the expense during manufacturing of applying two different types of adhesive to comprise field 32, then a single field is used even if ionic conductivity is not required to be present in the perimeter section of field 32 not contacting conductor plates 14 and 16.

Nonlimiting examples of hydrophilic adhesives useful in connection with the present invention include those compositions disclosed in U.S. Pat. Nos. 4,524,087 (Engel); 4,539,996 (Engel); 4,848,353 (Engel) and 5,133,356 (Bryan et al), ; 5,225,473 (Duan); 5,276,079 (Duan et al); 5,338,490 (Dietz et al); 5,362,420 (Itoh et al); 5,385,679 (Uy et al); copending and coassigned applications PCT Publication Nos. WO 95/20634 and WO 94/12585; and PCT patent application Ser. Nos. US95/17079 (Docket No. 51537PCT6A); US95/16993 (Docket No. 51290PCT8A); and US95/16996 (Docket No. 48381PCT1A), the disclosures of which are incorporated by reference herein. Further nonlimiting examples of hydrophilic adhesives that do not have ionically conductive properties but would be useful for the perimeter section of field 32 include U.S. Pat. Nos. 4,871,812 and 5,407,717 (both Lucast et al.); 4,981,903 and Re 34,958 (both Garbe et al.); 5,009,224 (Cole); 5,232,838 (Nelson et al.); and 5,270,358 (Asmus); PCT Publication WO 95/27016; and adhesives commercially available from the Medical Specialties Department of 3M Health Care, 3M Company, St. Paul, Minn., the disclosures of all of which are incorporated herein by reference.

Release liner

Release liner 34 can be any construction suitable for protecting the conductive adhesive 32 during shipping and handling while still releasing easily from the conductive adhesive at the time of use. One suitable liner is a 0.05 mm (0.002 inch) thick sheet of biaxially oriented polypropylene liner, commercially available as Daubert 164Z from Daubert Co. of Dixon, Ill.

Adhesive layers

In some presently preferred embodiments, adhesive layers 36 and 38 may be used for holding other components of the electrode 10 together. Nonlimiting examples suitable adhesives 36 and 38 include acrylate ester adhesives, and more particularly acrylate ester copolymer adhesives. Such adhesives are generally described in U.S. Pat. Nos. 2,973,826; Re 24,906; Re 33,353; 3,389,827; 4,112,213; 4,310,509; 4,323, 557; 4,732,808; 4,917,928; 4,917,929; and European Patent Publication 0 051 935, all incorporated herein by reference.

Lossy dielectric layer

The layer 26 of lossy dielectric material has the performance parameters identified above in association with the ultimate performance of electrode 10 to minimize the maximum rise in temperature of tissue of a patient during electrosurgical procedures.

The lossy dielectric layer 26 can occupy an area of the body contact portion 22 ranging from about 5% to about 70% and preferably from about 40% to about 60%.

The lossy dielectric layer 26 can be made from a material and be applied in a non-uniform thickness to result in an electrical impedance gradient from the center of the body contact portion 22 to the exterior edge 25 ranging from about 30% to about 90% of the maximum impedance at exterior edge 25, and preferably from about 50% to about 70% of the maximum impedance at exterior edge of body contact portion 22.

The layer 26 can have a maximum impedance/area at the exterior edge 25 of the body contact portion 22 of the electrode 10 ranging from about 0.387 $\Omega/129$ cm$^2$ to about 20 $\Omega/129$ cm$^2$ and preferably ranging from about 1 $\Omega/129$ cm$^2$ to about 8 $\Omega/129$ cm$^2$, as determined by use of a Schlumberger 1260 spectrum impedance analyzer, operating at a frequency of 500 KHz and a constant voltage of 60 mV (RMS), and subjected to a nulling file to subtract out the effects of leadwires, connecting clips, and test fixture. A dispersive electrode of approximately 129 cm$^2$ (20 in$^2$) is the approximate size of most commercially available dispersive electrodes.

The layer 26 can have a resistance component per unit area (R/area) of the complex impedance Z of from about 0.4 $\Omega/129$ cm$^2$ to about 5 $\Omega/129$ cm$^2$ at exterior edge 25 on the dispersive electrode 10. Preferably, the layer 26 can have a resistance component per unit area ranging from about 0.5 $\Omega/129$ cm$^2$ to about 1.4 $\Omega/129$ cm$^2$. These values were determined as done for the maximum impedance per unit area.

The layer 26 can have a reactance component per unit area (X/area) of the complex impedance of from about −0.5 $\Omega/129$ cm$^2$ to about −16 $\Omega/129$ cm$^2$ at exterior edge 25 on the dispersive electrode 10. Preferably, the layer 26 can have a reactance component per unit area ranging from about −2 $\Omega/129$ cm$^2$ to about −10 $\Omega/129$ cm$^2$, using the same testing method as above for resistance per unit area and impedance per unit area.

The layer 26 can have a tan $\delta$ ranging from about 0.14 to about 1.7 at exterior edge 25 on the electrode 10, when measured at 500 KHz and a signal amplitude of 60 mV (RMS). Desirably, the tan $\delta$ can range from about 0.2 to about 1.0 at exterior edge 25 on the electrode 10, when measured at 500 Hz and a signal amplitude of 60 mV (RMS). Preferably, the tan δ ranging from about 0.2 to about 0.7 at exterior edge 25 on the electrode 10, when measured at 500 Hz and a signal amplitude of 60 mV (RMS).

Layer 26 can be made from any lossy dielectric material that can be applied to body contact portion 22 and provide the performance parameters identified above for layer 26.

Layer 26 can be formed from an ink or paint on body contact portion 22 according to electrode manufacturing techniques known to those skilled in the art. It has been found particularly convenient to provide this material in the form of a paint, which can then be screen printed or sprayed in an appropriately shaped pattern onto the electrode 10 at the proper time during its fabrication. Oil-based enamels, commercially available as Cat. nos. 7776, 7790, 7730, 7727, and 7715 from Rust-oleum Corp. of Vernon Hills, Ill. are considered particularly suitable. Inks such as Summit UVII 300, UVII 800, and UVII 801 white inks, from Summit, Inc. of North Kansas City, Mo. and Werneke Ultrafuse UFR Green, #UFGUB0008 from Werneke, Inc. of Plymouth, Minn. can also be used. Additional information on the use of a lossy dielectric layer to reduce the heating caused by edge effect can be found in co-pending and co-assigned U.S. patent application Ser. No. 08/628,182, the entire disclosure of which is hereby incorporated by reference.

Method of Making Electrodes

Electrode 10 can be made using conventional tab/pad style electrodes as described in U.S. Pat. Nos. 4,352,359 (Larimore); 4,524,087 (Engel); 4,539,996 (Engel); 4,554, 924 (Engel); 4,848,348 (Carim); 4,848,353 (Engel); 5,012, 810 (Strand et al.); 5,133,356 (Bryan et al.); 5,215,087 (Anderson et al.); and 5,296,079 (Duan et al.), the disclosures of which are incorporated by reference herein. Generally, multiple layered electrode 10 can be assembled from rolls of starting materials for insulative electrically non-conductive backing 12, upon which is applied conductor plates 14 and 16, upon which is coated paints or inks to form lossy dielectric layer 26, upon which is coated or cured field 32 of hydrophilic, ionically conductive pressure sensitive adhesive. Alternatively, a sheet of lossy dielectric material of a desired geometrical shape can be laminated onto conductor plates 14 and 16.

Automated machinery can be employed to make electrode 10. One skilled in the art of making electrodes can select from a variety of machinery manufacturers and manufacturing techniques to minimize manufacturing expense and waste. Some types of machinery are disclosed in U.S. Pat. Nos. 4,715,382 (Strand); 5,133,356 (Bryan et al.); and copending, coassigned U.S. patent application Ser. No. 08/343,253 (Yasis et al.), the disclosures of which are incorporated by reference herein, and U.S. Pat. No. 5,352,315 (Carrier et al.).

Method of Monitoring Total Contact Impedances

Any electronic method suitable for "real time" monitoring of total contact impedances at two different frequencies in an electrical circuit is acceptable for use in the present invention. Because of the constant advances in electronics, no one manner of monitoring of total contact impedances can be identified as clearly superior to another. However, several known methods can be outlined as presently suitable for use in the present invention.

Electronics for the present invention can rely on software, hardware, or both to achieve a multi-frequency monitoring of total contact impedances of a biomedical electrode connected to both biomedical instrumentation and the skin of a patient.

Nonlimiting examples of ways to monitor total contact impedances of current flows can include electronic circuitry disclosed in the following U.S. Patents, but adapted by one skilled in the art for the purposes of this invention to monitor two different frequencies at various times: U.S. Pat. Nos. 5,422,567 (Matsunaga); 4,922,210 (Flachenecker et al.); 3,601,126 (Estes); 4,092,986 (Schneiderman); 4,281,373 (Mabille); 4,321,926 (Roge); 4,658,819 (Harris et al.); 4,727,874 (Bowers et al.); 4,860,745 (Farin et al.); 4,969,885 (Farin); and 4,102,341 (Ikuno et al.).

Usefulness of the Invention

Beyond the immediate utility to monitor lift of patient plates from skin of patients, this invention has a much broader application in other biomedical electrodes, or even beyond in other areas where additional information is desired about conduction across an interface.

For example, a biomedical electrode may be manufactured with a lossy dielectric coating located in certain areas that will "signal" whether those areas are effectively conducting electricity or have become disconnected in some way. The purpose of the lossy dielectric coating in such a biomedical electrode may not be to alter the current distribution in any way, but may simply serve as a way of "signaling" that certain areas of the electrode are indeed conducting electricity.

Because this invention employs the special properties of lossy dielectric components in an electrical interface, the invention uses a material that inhabits a curious "no man's zone" in that lossy dielectric surfaces are generally regarded as having the properties of a badly defective resistor or capacitor that is totally unusable for the purpose that either component is designed for. As such, this invention can be a novel adaptation of an electrical phenomena that had up until now been regarded as a failure mode of other common devices.

Biomedical electrodes of the present invention can be electrically connected to electrosurgical generators or cardiac stimulation devices to provide dispersive electrode connection or cardiac stimulation electrode connection, respectively. Electrosurgical generators are commonly available and known to those skilled in the art, such as devices marketed by Birtcher Medical Systems, Inc. of Irvine, Calif.; Aspen Surgical Systems, Inc. of Utica, N.Y.; and Valleylab, Inc. of Boulder, Colo. Cardiac stimulation devices for cardioversion, external pacing, and defibrillation are commonly available and known to those skilled in the art, such as devices marketed by Hewlett-Packard Corporation of McMinnville, Oreg.; Zoll Medical Corporation of Newton, Mass.; and Physiocontrol Corporation of Redmond, Wash. Any of these medical devices can be modified to include hardware and software embodiments of this invention to provide a measurement of the difference of phase angle to advantage according to this invention.

While not being limited to particular theory, the following explanation provides evidence of the unexpectedness of the present invention.

For a plain biomedical electrode comprising a conductor surface and a skin contacting agent such as a conductive adhesive, the total contact impedance is defined as the impedance between the conductor surface and the skin and/or tissues of the patient for the entire electrode as it is applied to the patient. This impedance is measured in ohms, rather than ohms/cm$^2$, because the contact impedance is always for the whole electrode surface, whatever that surface area might be.

Total contact impedance for an electrode can be approximated in terms of finite element analysis by a series of resistors wired together in parallel, with each resistor representing the resistance of a small, discrete area of the total conductor surface. For a biomedical electrode with a surface area of 100 cm$^2$, the total contact impedance could be represented by the sum of the resistances of 100 resistors wired in parallel, with each resistor representing the resistance of one unique and discrete square centimeter of the electrode's surface. The general equation for calculating the total impedance of a group of resistors wired in parallel is shown in Equation III:

$$1/R_{total} = 1/R_1 + 1/R_2 + 1/R_3 + 1/R_4 + \frac{1}{4} + 1/R_n \qquad \text{III}$$

For a conventional, plain biomedical electrode without any lossy dielectric coating, the impedance value for each $R_n$ will be equal, assuming that the conductor layer and adhesive layers are both of equal caliper and homogenous composition. For a plain biomedical electrode, the total contact impedance is inversely proportional to the number of elements of equal area used in the equation. Table 1 shows the calculation above done for a series of 1–10 finite elements, with each element having an resistance of 2 ohms. As can be seen, as the number of elements (of a fixed size) increases, the total contact impedance $R_{TOTAL}$ goes down. Conversely, as the number of elements is decreased, the total contact impedance will rise. The number of elements in this hypothetical example can be made smaller in one of two ways:

One can start out with an electrode of smaller surface area, or

One could partially peel back the current electrode to create a smaller contact area with the patient's skin.

TABLE 1

| Total No. of Elements | Resistance per Element | $R_{TOTAL}$ |
|---|---|---|
| 1 | 2 | 2.000 |
| 2 | 2 | 1.000 |
| 3 | 2 | 0.667 |
| 4 | 2 | 0.500 |
| 5 | 2 | 0.400 |

TABLE 1-continued

| Total No. of Elements | Resistance per Element | $R_{TOTAL}$ |
|---|---|---|
| 6 | 2 | 0.333 |
| 7 | 2 | 0.286 |
| 8 | 2 | 0.250 |
| 9 | 2 | 0.222 |
| 10 | 2 | 0.200 |

To demonstrate this hypothetical example in actual practice, a plain resistive electrode was made as follows: An electrode was constructed from a 99 cm² (15 square inches) of Aluminum foil having corners with a radius of 2.54 cm. A layer of conductive adhesive was prepared according to the following procedure. Into a 300 gallon kettle equipped with overhead stirrer and a cooling jacket was charged 562.8 pounds (255.5 kg) acrylic acid, 1.4 pounds (636 grams) 2,2-dimethoxy-2-phenyl acetophenone, 2.8 pounds (1273 grams) 4-(2-hydroxyethoxy)phenyl-(2-hydroxy-2-methylpropyl)ketone, 1.12 pounds (508 grams) methylene bis(acrylamide), 1251.6 pounds (568.2 kg) glycerin, 2.8 pounds (1273 grams) guar gum, and 459.6 pounds (208.7 kg) deionized water. To the well stirred solution was charged 499.8 pounds (226.9 kg) 50% aqueous NaOH portionwise maintaining the batch temperture below 38° C. The hydroxide line was rinsed into the kettle with an additional 18 pounds (8.2 kg) deionized water and stirred for 30 minutes to yield coater-ready precursor. The precursor was coated onto the foil side of a polyester/aluminum foil laminate at 23 mil (0.6 mm) thick, overlaminated with a siliconized polyester liner, and passed through a curing chamber consisting of banks of fluorescent "black" lights, exposing the material to an intensity of 1.9 mW/sqcm and a total dose of 315 mJ/sqcm. The layer of conductive adhesive so prepared was then placed over the whole square of the electrically conductive surface.

Next, a series of four 45° diagonal lines was scribed on the back of two corners of the plate, starting 5mm in from the corner and repeating every 5 mm. This electrode was placed on a human right anterior thigh. For comparison, a commercial patient plate (3M No. 7149 Minnesota Mining and Manufacturing Company, St. Paul, Minn.) was placed on the human's left anterior thigh to act as a source of electricity flowing from another site to the location on the body where the dispersive electrode was located. An impedance scan utilizing a voltage of 60 mV was then made from a frequency of 1 MHz down to 1 Hz using a Schlumberger 1260 spectrum impedance analyzer. Next, the corner of the plate outside of the farthest line was cut off to simulate peeling the electrode back a very precise distance (of 5 mm or 0.197"), and another impedance scan was run. Then the remaining corner of the plate outboard of the second line was cut off, and another scan was run. This process was repeated a total of 8 times until a total of 2 cm. of material was cut off two corners of the plate. Next, a calculation was made of how much surface area was removed each time more of one of the corners was cut off. Table 2 shows the results.

TABLE 2

| | Area in single cut | % of total area in single cut | Cumulative % of total plate cut off |
|---|---|---|---|
| 1st cut | 0.153 | 1.010 | 1.010 |
| 2nd cut | 0.276 | 1.823 | 2.833 |
| 3rd cut | 0.353 | 2.331 | 5.164 |

TABLE 2-continued

| | Area in single cut | % of total area in single cut | Cumulative % of total plate cut off |
|---|---|---|---|
| 4th cut | 0.429 | 2.833 | 7.998 |
| 5th cut | 0.153 | 1.010 | 9.008 |
| 6th cut | 0.276 | 1.823 | 10.831 |
| 7th cut | 0.353 | 2.331 | 13.162 |
| 8th cut | 0.429 | 2.833 | 15.995 |

Finally, a chart was drawn for the contact impedance of the plate at 1 MHz, 100 KHz, and 10 KHz, and was plotted against the cumulative % of surface area lost as the plate was progressively cut down. FIG. 3 shows the results, and as can be seen, there is an increase in the impedance at all three frequencies as the size of the plate is reduced. For convenient comparison to some trend lines calculated later on more significant data, 2nd order polynomial fits of the data are also shown on FIG. 3.

To further correlate this data with a theoretical model, the impedance of a 15 square inch plain Al foil plate was measured on a metal ground plane, and found to be 0.57 ohms. A calculation was then made based on dividing this 15 square inch area up into 200 elements (i.e., unit area) of 0.075 square inches each, and by use of back calculation with the equation for the sum of parallel resistive elements, the impedance for each element was found to be 114 ohms. The appropriate number of resistive elements were then subtracted to correspond to the surface area that was actually cut off in the laboratory experiment, and the impedance was calculated for the finite element model with this smaller number of elements. Finally, this data was "aligned" on FIG. 3 with the 1 MHz data by adding 67.1 ohms to each calculated impedance so that the contact impedance of the 15 square inch plate on the metal ground plane would be the same as the impedance of that plate on the human. (In other words, the impedance of the human was assumed to be 67.1 ohms.)

The calculated data is shown below in tabular form of Table 3. The finite element model and the actual data agreed as the plain metal foil plate was progressively cut away. This fit was just as good if the intercept values of the other two lines (80.27 or 116.00) were added to the calculated data.

TABLE 3

| Total # of Elements | Resistance per Element | $R_{TOTAL}$ | $R_{TOTAL}$ + 67.1 |
|---|---|---|---|
| 200 | 114 | 0.57000 | 67.670 |
| 198 | 114 | 0.57576 | 67.676 |
| 194 | 114 | 0.58763 | 67.688 |
| 190 | 114 | 0.60000 | 67.700 |
| 184 | 114 | 0.61957 | 67.720 |
| 182 | 114 | 0.62637 | 67.726 |
| 178 | 114 | 0.64045 | 67.740 |
| 174 | 114 | 0.65517 | 67.755 |
| 168 | 114 | 0.67857 | 67.779 |

This meant that the slight increase in impedance with decreasing surface area was not dependent on frequency. This was consistent with the fact that conventional plates using only Al foil and conductive adhesive are totally resistive in nature, since for an impedance value which is made up totally of resistance, (rather than resistance and reactance as is present with lossy dielectric material) there is no change in impedance as the frequency is varied.

The reason for the differences in total contact impedance between the three frequencies is due to the fact that human tissue is not purely a resistive conductor, so as the frequency of the current becomes lower the impedance of human tissue rises proportionately. This is partly why the contact impedance of a patient plate may be less than 100 ohms at 1 MHz, while the contact impedance of an ECG electrode may be 500 Kilohms at 10 Hertz.

Figure 4:
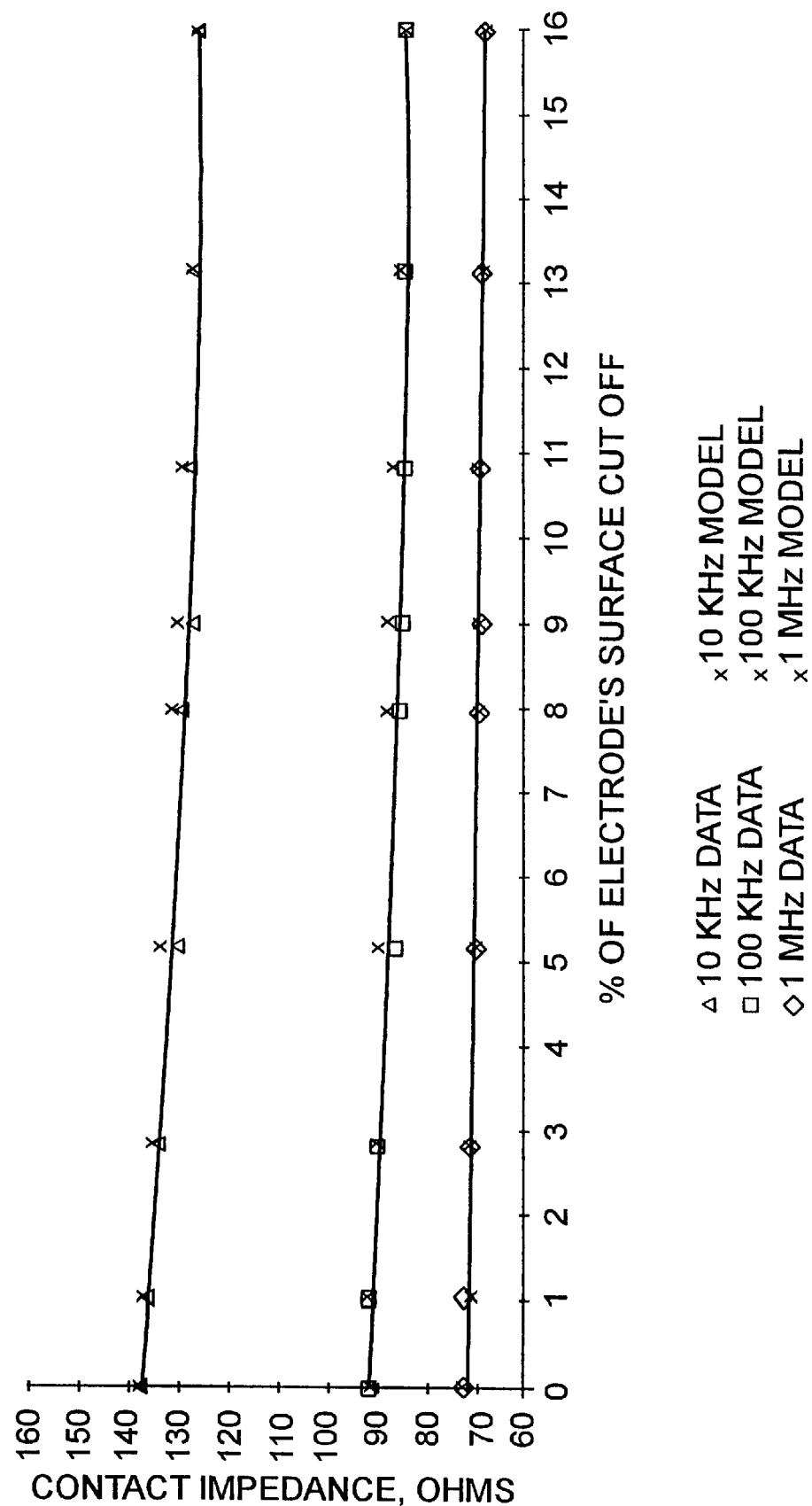
FIG. 4 is a graph showing total contact impedance vs. area of electrode surface for a lossy dielectric biomedical electrode, both actual and theoretical data, using three different frequencies, demonstrating the differing rate of decrease in the total contact impedances at the various frequencies, as the amount of electrode surface area was reduced.

Next, this experiment was repeated for a Netherly patient plate prepared according to Example 56 of copending, coassigned, U.S. patent application Ser. No. 08/628,182 (Netherly et al.) except that the lossy dielectric material was Werneke Ultrafuse UFR Green, # UFGUB0008 from Wemeke, Inc. of Plymouth, Minn. with a coating in three ring concentric stepped (0.10 inch wide) shading construction within the perimeter of the plate, and the data was plotted the same way and shown in FIG. 4. FIG. 4 demonstrates shows there is a drop in impedance as the corners of the patient plate are removed.

Moreover, it is evident that this decrease is not the same for the three frequencies shown. Thus, the method of present invention employs impedance measurements with interrogation at at least two different frequencies. The data in FIG. 4 shows three different frequencies used and total contact impedance as the percentage of the patient plate being removed from contact with a patient's skin was increased.

To explain this performance, it must first be understood that not all points on a Netherly plate (which has a coating of lossy dielectric material at its corners and edges) have the same impedance. As a matter of fact, the entire point of the Netherly plate is to create a higher impedance at the corners and edges of the plate in order to lower the naturally high current densities that occur at these locations, and it has been established in extensive clinical testing that this goal is indeed met. Secondly, since this higher impedance is achieved by use of a lossy dielectric coating rather than a material which is either purely resistive or purely capacitive, the use of a finite element model based purely on parallel resistances is not appropriate.

To briefly review, impedance is a vector quantity made up of resistance and reactance scalar terms. The impedance Z of the lossy dielectric material is made up of about 4 times as much Reactance X as Resistance R. Since the impedance of the lossy dielectric material is primarily due to the Reactance, which is inversely proportional to the frequency, the impedance varies greatly with frequency.

The present invention has unexpectedly found edge effect present with all biomedical electrodes as they function while they are attached to human tissue, since edge effect is not dependent on the level of current used. This means that the current distribution will preferentially cluster at the corners and edges of a patient plate to the same degree for both a multi-hundred volt 1 amp surgical cutting current and a tiny 60 mV microampere sensing current from a Schlumberger 1260 impedance analyzer. When an impedance measurement is made on a patient plate while it is applied to human tissue, then, it is a fact that the sensing current is preferentially concentrated on the corners and edges of the plate. This means that the contact impedance of the plate as a whole is influenced more by the impedance at the edges and corners of the plate than the impedance at the center of the plate, since there is more electrical flow at the corners and edges of the plate than in the middle of it.

Now, for a normal A1 foil plate where the entire conductive surface is isotropic (same impedance at every point on the plate...) this makes no difference, since the impedance at the corners is the same as in the middle of the plate. (Mathematically, this would be like taking the average of a group of numbers that all had the exact same value: There would be no difference between the average and any one of the individual numbers.) When the corner of a plain A1 foil plate is lifted off a patient's skin, then, the only effect that is noted is a slight increase in impedance that is due to the overall reduction in surface area. The fact that it was the corner that was lifted rather than the center of the plate cannot be detected, since per unit area both the corner and the center of the plate have the same impedance, even if the current density at these two locations is very different.

For a Netherly patient plate having a lossy dielectric material, the impedance is not the same for the corners and the center of the plate, and the makeup of the total contact impedance is also quite different. The impedance at the center of the plate (where there is bare metal) is totally resistive, while the impedance in the lossy dielectric areas at the edges and the corners of the plate is about 4 times more capacitive (in the form of reactance) than resistive. While the lossy dielectric serves to force the current (either surgical or impedance sensing) off the corners quite effectively, it is still a fact that a majority of the current is passing through the lossy dielectric portion of the plate. This means that as the contact impedance of a Netherly patient plate with a lossy dielectric material is measured on a human being, the concentration of sensing current in the high impedance areas of the plate is having a disproportionately large effect on the average impedance measurement for the whole plate.

As noted above, this is of no consequence for the measurement of contact impedance with a plain A1 foil plate, for the reasons already stated. For a Netherly lossy dielectric patient plate, however, the impedance in the patient's tissues (which is the cause of corner and edge effect) forces more current through the high impedance pathways at the corners and edges of the Netherly lossy dielectric patient plate.

In other words, due to the high impedance in the patient's tissues across a distance of several inches, the edge and corner effect is overwhelming the natural tendency for either the surgical or impedance sensing current to follow the "normal" path of least resistance through the bare metal in the center of the plate. It is for this reason that a finite element model of a patient plate based on parallel resistances can simulate the performance of a normal A1 foil plate so well, while it totally fails to duplicate the performance of a lossy dielectric patient plate.

As a consequence of this "forced" high impedance current flow through the corners and edges of a lossy dielectric patient plate, one would expect that the impedance measurement on a human test subject would be higher for that plate than for a corresponding 15 square inch A1 foil plate. This is in fact the case, and the impedance data for both plates at three different frequencies shown in Table 4 below, as well as the difference between the two impedances.

TABLE 4

| Frequency (Hz) | Lossy Dielectric Patient Plate Impedance ($\Omega$) | A1 Foil Patient Plate Impedance ($\Omega$) | Difference in Impedances ($\Omega$) |
| --- | --- | --- | --- |
| $10^6$ | 71.62 | 67.45 | 4.17 |
| $10^5$ | 90.92 | 80.58 | 10.34 |
| $10^4$ | 137.37 | 116.57 | 20.80 |

The present invention unexpectedly has found that the difference between the two impedances is not constant and that this difference is used in the method of the present invention.

Based on the previous explanation and data, a finite element model was constructed which fairly well duplicated the experimental performance of the lossy dielectric patient plate at all three frequencies. The model was made up of 200 elements as before, and those elements that represented the bare metal in the center of the plate are still treated as simple parallel resistors. Based on the total area of bare metal in a 15 square inch solid (not split) plate being almost exactly 9 square inches, 119 out of the 200 elements were represented as being simple resistive elements. The other 81 elements were represented as being a combination of resistive and reactive elements, and the resistive part of each of these lossy dielectric elements was allowed to interact mathematically with the bare metal elements in the center of the plate. The reactive part of these 81 elements, however, were treated differently in the calculation. To simulate the "forcing" of the sensing current through the high impedance lossy dielectric areas, the reactances were treated as being in series rather than parallel. (In other words, they were cumulatively added up to a total of however many reactive elements there were for that simulation.) For the initial case where all 81 elements were present, the sum of this reactance is approximately equal to the difference between two of the total contact impedances shown above. In equation form, then, Equation IV below was developed to simulate the performance of the present invention.

$$Z_{total} = X_1 + X_2 + X_3 + \ldots + X_n 30\ 1/(1/R1d_1 + 1/R1d_2 + \ldots + 1/R1d_n + 1/Rm_1 + \ldots + 1/Rm_{119}) \quad \text{IV}$$

In the above Equation IV, X represents the Reactance of the lossy dielectric elements, R1d represents the Resistance of the lossy dielectric elements, and Rm represents the resistance of the bare metal elements.

When this model was initially constructed, the ratio of reactance to resistance was kept at a constant ratio of 4 since this is what is seen in the electrical measurement of a uniform layer of lossy dielectric ink determined as described above. This resulted in $R_{LD}$ values that were between 2 and 10 times larger than the value of 114 ohms selected for the bare metal, which seemed to make sense on a physical level if one were comparing the purely resistive component of the lossy dielectric coating to the resistance of the bare metal. After this the reactances were adjusted to get the ends of the modeled data curves to line up with the real data, and the overall fit was passable. In an attempt to get the middle of the modeled curves to "sag" downwards to more closely agree with the experimental data, some other $R_{LD}$ values were chosen at random to see how this would affect the data. Surprisingly enough, the fit improved as the $R_{LD}$ values were made smaller than the $R_M$ values, and the fit improved until an $R_{LD}$ value of 0.00001 ohms was reached.

While it is quite unexpected to consider a system where the resistance of a lossy dielectric element was 7 orders of magnitude smaller than a bare metal element, when the full sum of all the resistive terms was considered, there was an interesting physical interpretation of the resulting calculation. If a purely resistive plate were to be constructed where the impedance in the center of the plate was 114 ohms/unit of area, while the impedance around the corners and edges of the plate was set at 1 ohm (or less)/unit of area, the current would be strongly forced to the corners and edges of the plate.

In conclusion, then, when the values of this model were adjusted to give the best fit to the experimental data, the concept of a "forced" high impedance pathway appeared to drop out of the model as a matter of course.

The actual calculations are shown below in Table 4 for all three frequencies, and FIG. 4 also shows the modeled data superimposed on the graph of the original experimental data.

TABLE 4

| Total # of Lossy Dielectric Elements | 1 MHz Reactance per Element | Resistance per Element | Total # of Bare Metal Elements | Resistance per Element | $Z_{TOTAL}$ |
|---|---|---|---|---|---|
| 81 | 0.0545 | 1 | 119 | 114 | 4.427 |
| 79 | 0.0545 | 1 | 119 | 114 | 4.318 |
| 75 | 0.0545 | 1 | 119 | 114 | 4.101 |
| 71 | 0.0545 | 1 | 119 | 114 | 3.883 |
| 65 | 0.0545 | 1 | 119 | 114 | 3.558 |
| 63 | 0.0545 | 1 | 119 | 114 | 3.449 |
| 59 | 0.0545 | 1 | 119 | 114 | 3.232 |
| 55 | 0.0545 | 1 | 119 | 114 | 3.015 |
| 49 | 0.0545 | 1 | 119 | 114 | 2.690 |

| Total # of Lossy Dielectric Elements | 100 KHz Reactance per Element | Resistance per Element | Total # of Bare Metal Elements | Resistance per Element | $Z_{TOTAL}$ |
|---|---|---|---|---|---|
| 81 | 0.19 | 1 | 119 | 114 | 15.402 |
| 79 | 0.19 | 1 | 119 | 114 | 15.022 |
| 75 | 0.19 | 1 | 119 | 114 | 14.263 |
| 71 | 0.19 | 1 | 119 | 114 | 13.504 |
| 65 | 0.19 | 1 | 119 | 114 | 12.365 |
| 63 | 0.19 | 1 | 119 | 114 | 11.986 |

| Total # of Lossy Dielectric Elements | 1 MHz Reactance per Element | Resistance per Element | Total # of Bare Metal Elements | Resistance per Element | $Z_{TOTAL}$ |
|---|---|---|---|---|---|
| 59 | 0.19 | 1 | 119 | 114 | 11.227 |
| 55 | 0.19 | 1 | 119 | 114 | 10.468 |
| 49 | 0.19 | 1 | 119 | 114 | 9.330 |

| Total # of Lossy Dielectric Elements | 10 KHz Reactance per Element | Resistance per Element | Total # of Bare Metal Elements | Resistance per Element | $Z_{TOTAL}$ |
|---|---|---|---|---|---|
| 81 | 0.34 | 1 | 119 | 114 | 27.552 |
| 79 | 0.34 | 1 | 119 | 114 | 26.872 |
| 75 | 0.34 | 1 | 119 | 114 | 25.513 |
| 71 | 0.34 | 1 | 119 | 114 | 24.154 |
| 65 | 0.34 | 1 | 119 | 114 | 22.115 |
| 63 | 0.34 | 1 | 119 | 114 | 21.436 |
| 59 | 0.34 | 1 | 119 | 114 | 20.077 |
| 55 | 0.34 | 1 | 119 | 114 | 18.718 |
| 49 | 0.34 | 1 | 119 | 114 | 16.680 |

To use this phenomena to detect small amounts of corner lift with a lossy dielectric patient plate, a CQM circuit can be constructed to monitor the total contact impedance of the patient plate at two widely spaced frequencies, such as I MHz and 10 KHz) at various intervals of time. If a drop in impedance were noted at 10 KHz that was not seen at 1 MHz, this would be conclusive evidence that one or more corners of the Netherly plate was becoming detached from the patient. If a downward drift in both frequencies were noted, this would be interpreted as the normal process of the plate becoming more securely adhered to the patient with time, and thus the two phenomena could be easily differentiated by the CQM circuit. This would also apply to any impedance rise associated with extensive cooling of the patient's tissues, which occurs commonly with cardiovascular cases.

Unlike the detection of plate lift by phase angle shift as disclosed in copending, coassigned U.S. patent application Ser. No. 08/832835 (Atty. Docket No.53324USA5A), which both works better for split plates, and is also much easier to implement for a split design than solid design, this dual impedance method can work better for solid plates than split ones. In addition, all CQM generators are already set up to monitor impedance at one frequency between 10 KHz and 1 MHz. While their present circuit design does this by use of a small, clean AC signal that is only activated when the generator is not actively cutting, there is known in the art to be able to detect impedance changes "through" the noise of the actual surgical arc itself. In order to implement automatic coagulation in either the monopolar or bipolar mode with a generator, this technical obstacle must be overcome, and both the Valleylab FX and the Erbe ICC 350 generators currently offer this modality with their systems. One skilled in the art of circuitry design can include the benefits of Equation I above into the CQM generator to establish both an apparatus for the present invention and the means to implement the method of the present invention using the teachings of the U.S. Pat. Nos. U.S. Pat. Nos. 5,422,567 (Matsunaga); 4,922,210 (Flachenecker et al.);3,601,126 (Estes); 4,092,986 (Schneiderman); 4,281,373 (Mabille); 4,321,926 (Roge); 4,658,819 (Harris et al.); 4,727,874 (Bowers et al.); 4,860,745 (Farin et al.); 4,969,885 (Farin); and 4,102,341 (Ikuno et al.).

One advantage of the present method over the method using a shift in phase angle is that the magnitude of the impedance change that must be detected is considerably larger than the magnitude of the phase shift that must be detected. However, it is an option of the present invention to use both methods for cross-correlation if so desired. For phase shift detection a precision of +0.1 degrees (out of 360) is desirable, while for impedance detection a precision of 1 ohm (out of 100) at 1 MHz and/or a precision of 3 ohms (out of 200) at 10 KHz is desirable. Finally, measurement of impedance changes at two frequencies can be viewed as a much more "static" process, compared to the challenge of measuring small shifts in the phase angle of an alternating current that is changing phase at the rate of 180,000,000 degrees (360×500 KHz) per second.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A method of detecting loss of contact between a biomedical electrode and skin of a patient, comprising the steps of:

(a) detecting total contact impedance of the electrode using two different frequencies to establish two initial total contact impedances;

(b) detecting two total contact impedances of the electrode using the same frequencies as in step (a) at at least one later time to establish two differences in total contact impedance, one difference for each frequency; and (b) sounding an alarm when the ratio of change of the contact impedances exceeds a predetermined amount.

2. A method of quantifying lift off of a biomedical electrode from skin of a patient, by the use of the equation:

$$Degree\ of\ Lift = (Z_{f1t0} - Z_{f1t1})/Z_{f2t0} - Z_{f2t1})$$

where Z denotes a total contact impedance of the biomedical electrode, f1 denotes a first impedance measurement frequency, f2 denotes a second impedance measurement frequency, t0 denotes a first (or initial) impedance measurement time, and t1 denotes a impedance measurement at some later time, comprising the steps of (a) measuring two initial total contact impedances using two different frequencies, (b) measuring two later time total contact impedances using the same two frequencies as in step (a) and using the equation to obtain a ratio of change of the two total contact impedances; and (c) sounding an alarm when the ratio of change of the two total contact impedances exceeds a certain set value.

3. A method of determining the amount of skin contact between a biomedical electrode and skin of a patient, comprising the steps of:

(a) measuring the ratio of the change of two total contact impedances, measured at different frequencies, over time of an energized biomedical electrode; and (b) sounding an alarm when the ratio of the change of the total contact impedances over time exceeds a predetermined amount.

4. An apparatus for detecting loss of contact between a biomedical electrode and skin of a patient, comprising:

(a) a biomedical electrode having an electrical conductor having at least a portion thereof having lossy dielectric properties; and (b) means for measuring contact impedance at two different frequencies;

(c) means for detecting when a ratio in the change of total contact impedances measured at two different frequencies over time exceeds a predetermined amount.

* * * * *